United States Patent [19]

Wolff et al.

[11] Patent Number: 5,416,131

[45] Date of Patent: May 16, 1995

[54] ARTICLE WITH A COATING HAVING FRICTION-REDUCING PROPERTIES IN WET CONDITION AS WELL AS A METHOD FOR THE PRODUCTION OF SUCH A COATED ARTICLE

[75] Inventors: Per Wolff, Birkerod; Inge M. Holmskov, Slangerup, both of Denmark

[73] Assignee: Uno Plast A/S, Undested, Denmark

[21] Appl. No.: 73,471

[22] Filed: Jun. 9, 1993

[30] Foreign Application Priority Data

Jun. 10, 1992 [DK] Denmark .................... 0768/92

[51] Int. Cl.⁶ .................... B05D 3/00; B32B 9/04; B32B 27/40
[52] U.S. Cl. .................... 523/105; 427/2.12; 427/393.5; 427/2.28; 427/2.3; 428/411.1; 428/424.6; 424/78.24; 524/507; 524/530; 524/401; 604/265
[58] Field of Search .................... 604/265; 427/2, 393.5; 424/78.24; 428/411.1, 424.6; 523/105; 524/507, 530, 401

[56] References Cited

U.S. PATENT DOCUMENTS

| | | | |
|---|---|---|---|
| 4,100,309 | 7/1978 | Micklus et al. | 427/2 |
| 4,143,423 | 3/1979 | Stenlieb | 427/2 |
| 4,473,670 | 9/1984 | Kessidis | 523/105 |
| 4,589,873 | 5/1986 | Schwartz et al. | 427/2 |
| 4,642,267 | 2/1987 | Creasy et al. | 428/413 |
| 4,666,437 | 5/1987 | Lambert | 604/265 |
| 4,835,003 | 5/1989 | Becker et al. | 427/2 |
| 4,906,237 | 3/1990 | Johansson et al. | 604/262 |
| 4,990,357 | 2/1991 | Karakelle et al. | 427/2 |
| 5,084,315 | 1/1992 | Karimi et al. | 427/2 |
| 5,160,790 | 11/1992 | Elton | 604/265 |

FOREIGN PATENT DOCUMENTS

| | | | |
|---|---|---|---|
| 159018 | 10/1983 | Denmark | A61M 25/00 |
| 1600963 | 10/1981 | United Kingdom | B32B 27/06 |
| WO90005162 | 5/1990 | WIPO | C08J 7/04 |

*Primary Examiner*—Peter A. Szekely
*Attorney, Agent, or Firm*—Cushman Darby & Cushman

[57] ABSTRACT

A method of producing an article with a coating having friction-reducing properties in wet condition, the coating including a binder (a), a hydrophilic polymer (b), as well as an osmolality-increasing compound (c), where the osmolality-increasing compound (c) is applied in a condition different from a water-based dissolved condition, preferably in a non-dissolved, solid condition, as well as an article with a coating having friction-reducing properties in wet condition, the coating comprising a binder (a), a hydrophilic polymer (b), and an osmolality-increasing compound (c) in form of particles of a size of maximum 50 μm. The method can be performed in a simple and fast manner without involving a time-delaying evaporation of water, and the article is remarkable for the osmolality-increasing compound being uniformly dispersed in the coating.

16 Claims, No Drawings

ARTICLE WITH A COATING HAVING FRICTION-REDUCING PROPERTIES IN WET CONDITION AS WELL AS A METHOD FOR THE PRODUCTION OF SUCH A COATED ARTICLE

TECHNICAL FIELD

The present invention relates to an article with a coating having friction-reducing properties in wet condition, this coating comprising a binder (a), a hydrophilic polymer (b), and an osmolality-increasing compound (c), to a method for the production of such an article, to a coating material to be used by the production of the article, as well as to the use of an osmolality-increasing compound (c) in a condition different from a water-based dissolved condition, in such a coating material.

The invention relates in particular, but not exclusively to articles of the above type to be used in connection with surgery, therapy, or diagnostic methods, such as articles to be inserted in a body cavity, such as catheters, guide wires, wound drains and fibre-optical articles. These articles can be made of plastics, such as PVC or polyurethane, or of metal.

BACKGROUND ART

Several examples of these articles are known, such as catheters having a friction-reducing coating. In connection with catheters, the presence of the friction-reducing coating causes the surface of the catheter to be slippery and lubricating when the catheter is dipped into an aqueous, optionally saline solution prior to the insertion into a body cavity or when the catheter is contacted with an aqueous body liquid at the insertion into the body cavity. Thus, the discomfort experienced by the patient when the catheter is inserted into and removed from the body cavity is considerably reduced. The risk of damaging sensitive tissue in connection with the use of the catheter is at the same time considerably reduced.

The literature discloses several examples of coatings of the above type, in which the binder is based on polyurethane and the hydrophilic polymer is based on poly-(N-vinyllactam), cf. for instance GB-PS No. 1,600,963 (Micklus et al.), U.S. Pat. No. 4,666,437 (Lambert), U.S. Pat. No. 4,642,267 (Creasy et al.), and WO publication No. 90/05162 (Uno Plast A/S). In addition, Danish printed accepted application No. 159,018 (Lambert) discloses coatings based on an interpolymer of hydrophilic polyethyleneoxide and hydrophobic polyurea.

The friction-reducing coatings based on a hydrophilic coating have a much lower coefficient of friction in a wet condition than in a dry condition. It turned out, however, that such hydrophilic coatings may have a tendency to dry out, with the result that the article is insufficiently hydrophilic and that the coefficient of friction is increased.

Thus, tests on hydrophilic polymer coatings on various substrates have shown that when an article coated with a hydrophilic polymer coating is dipped into water, the coating is well wetted, but a high risk exists of the polymer coating losing its water content when contacted with the mucosa or the like due to the difference in the osmotic potential between the hydrophilic coating and the mucosa. The mucosa has a higher osmotic potential, i.e., a higher concentration of salt than the hydrophilic coating, with the result that the water leaves the hydrophilic layer and enters the mucosa, whereby the difference in the concentrations of salt is equalized. It is obvious that such a drying out involving an increased coefficient of friction can be highly unpleasant, such as when the catheter is to be removed.

A solution of this problem is described in U.S. Pat. No. 4,906,237 (corresponding to EP-PS No. 217,771 and Danish Pat. Application No. 4532/86; Johansson et al.), in which it is suggested to treat the polymer coating with a solution containing at least 2% salt, mono or disaccharide or a sugar alcohol, whereafter the solvent is evaporated from the solution. Such a treatment ensures the presence of an osmolality-increasing compound in the hydrophilic coating, whereby the above difference in the osmotic potentials in the coating and the surrounding mucosa is avoided. The suggested treatment with a solution followed by evaporation of the solvent, usually water, is, however, a time-consuming process with respect to production because the evaporation of water is a difficult and time-consuming process step for several reasons. Thus, water is per se a solvent being relatively difficult to volatilize, having a high boiling point, and requiring an extensive supply of evaporation heat. In addition, the added osmolality-increasing compound involves lowering of the vapour pressure, and the volatility of the water is accordingly additionally reduced. Finally, the hydrophilic coating binds and retains the water in the coating. During the step of the drying process, in which only a minor amount of water is left in the coating, the coating becomes adhesive, which involves further difficulties concerning the handling of the coated article which, of course, must be completely dry and non-adhering at the end of the process.

The articles coated by the method of Johansson et al. are furthermore encumbered with the drawback that the crystallization or the precipitation of the osmolality-increasing compound cannot be controlled, and the crystallization or precipitation is accordingly dictated by the conditions prevailing during the drying process after the application of the compound (c) in the dissolved condition. During the crystallization or the precipitation, the process is thus subject to arbitrary conditions caused by an irregular crystallization speed or precipitation speed and a non-uniform diffusion of the dissolved compound during the application performed by way of dipping for a long period, such as one hour.

Thus, a demand exists for a method of producing articles with coatings of the above type where the method is less complicated and less time-consuming with respect to the productional technique, and where the resulting coatings maintain a low friction when the article has been inserted into a body cavity, and in which the osmolality-increasing compound is more uniformly dispersed in the coating.

BRIEF DESCRIPTION OF THE INVENTION

In satisfaction of the above demand a method of producing an article with a coating having friction-reducing properties in wet condition, in which the coating comprises a binder (a), a hydrophilic polymer (b), as well as an osmolality-increasing compound (c), is according to the invention characterised by applying the osmolality-increasing compound (c) in a condition different from a water-based dissolved condition, preferably in a non-dissolved, solid condition.

The above application of the osmolality-increasing compound without using water for dissolving the compound ensures a considerable simplification of the production process compared, for instance to the technique disclosed by U.S. Pat. No. 4,906,237 (Johansson et al.), in which the osmolality-increasing compound is applied in form of a usually aqueous solution, usually in a separate process step where the solvent is evaporated after the application, which presents a time-consuming process step to the process.

A further advantage is found in the fact that the compound (c) is uniformly dispersed in a controlled manner across the surface of the coating, as it is no longer necessary to depend on uncontrollable conditions during the evaporation of a solvent from the compound (c).

Yet another advantage is found in the fact that the osmolality-increasing compound, such as sodium chloride, is not used in an aqueous solution, whereby problems of corrosion of the used equipment are reduced or avoided.

According to a preferred embodimemt of the method according to the invention, the osmolality-increasing compound (c) is applied in form of a fine-grained, solid product of a particle size of a maximum of 50 $\mu$m, preferably maximum 30 $\mu$m, especially a maximum 20 $\mu$m. Such a small particle size ensures uniform dispersion of the compound (c), and that particles of the compound (c) do not form ruggednesses in the surface of the coating.

The osmolality-increasing compound (c) may advantageously be made by way of crushing or grinding large crystals, whereby an edged structure is ensured. It turned out that a suspension of such particles possesses a surprisingly good stability.

According to an embodiment of the invention, the osmolality-increasing compound is advantageously applied in form of a solid powder by way of powdering.

According to another embodiment, the osmolality-increasing compound may be applied in form of a suspension or an emulsion in an organic solvent, in which the compound is insoluble. In this case the particles of the compound (c) are uniformly dispersed across the entire coating as discreet particles. In case of solid particles, the major portion of the crystal structure is determined prior to the coating process. Even when an additional, uncontrolled growth of crystals takes place during or after the coating process, the extent thereof is, however, restricted and has no essential effect on the advantageous properties of the coating.

In the latter case, the osmolality-increasing compound may advantageously be applied together with one or more of the applied coating materials containing binder (a) and hydrophilic polymer (b). In this manner, the osmolality-increasing compound can be applied without increasing the number of coating steps.

According to a particular embodiment of the invention, the hydrophilic polymer (b) or a portion thereof may also be applied in a suspended, undissolved condition, In this manner, it is possible to use a wide range of hydrophilic polymers as it is no longer necessary to use hydrophilic polymers being soluble in the same solvent as the binder. Such a method allows also a control of the structure of the coating, such as with a uniform dispersion of discrete particles of hydrophilic polymer together with discrete particles of the compound (c) in a matrix of binder, this matrix optionally also containing a portion of the hydrophilic polymer applied in dissolved condition, When the osmolality-increasing compound (c) is applied as an integrated part of one or more coating material layers, the following procedure may advantageously be followed. Each coating material layer containing the compound (c) is applied in form of two separate portions which are mixed together immediately before the application, in which the first portion comprises the binder (a) dissolved in an organic solvent and the hydrophilic polymer (b) dissolved or dispersed in an organic solvent, and in which the second portion comprises the osmolality-increasing compound (c) suspended in an organic solvent in which the osmolality-increasing compound is insoluble, preferably the same solvent as the solvent for the components (a) and (b).

In the latter case, the suspension may also contain undissolved hydrophilic polymer in suspended condition.

The method according to the invention may particularly advantageously be performed by means of the osmolality-increasing compound (c) in form of particles having a particle size of a maximum of 50 $\mu$m, preferably, a maximum of 30 $\mu$m, and especially a maximum 20 or 15 $\mu$m. It turned out surprisingly, that the use of a particle size below the above specified limits ensures a very stable suspension in which the particles can stay dispersed in the coating material for an entire working-day. One of the reasons for the latter effect is perhaps that the production of the particles by way of crushing or grinding results in edged particles. In addition it is ensured that the small particles do not settle as small roughnesses in the completed coating surface, which might otherwise involve an increased friction.

According to a particularly advantageous embodiment of the invention, a coating material is used which contains 4 to 16 parts by weight of hydrophilic polymer (b) per part by weight of binder (a). Such a relatively low amount of binder (a) compared to previously used ratios turned out to be possible, with the result that, on one hand, a sufficient binding to the article is obtained and, on the other hand, a high degree of hydrophility in the coating is obtained.

The amount of osmolality-increasing compound (c) added to the coating may advantageously be 10 to 40% by weight calculated relative to the sum of the components (a) plus (b). The amount of the osmolality-increasing compound (c) is adjusted to the use of the article coated with the friction-reducing coating. When the wetting before use is performed by means of a low and known amount of water, it is usually possible to use 10 to 25% by weight of component (c). In connection with catheters, 20 to 30% by weight of the compound (c) is preferably used, calculated relative to the sum of the components (a) plus (b).

It turned out to be possible by application of a single layer of coating to obtain an excellently adhering coating with the desired friction-reducing effect in a wet condition, by combining the above specified amount of hydrophilic polymer (b) of 4 to 16 parts by weight per part by weight of binder (a) and a content of the osmolality-increasing compound of 10 to 40% by weight relative to the sum of the components (a) plus (b). This embodiment presents a considerable improvement with respect to the productional technique compared to the method exemplified in U.S. Pat. No. 4,906,237 (Johansson et al.), in which the first step involves application of binder in form of a trimerised hexamethyleneisocyanate of the biuret type, dissolved in methylene chloride by a short dipping and drying. Subsequently, the second step involves application of a hydrophilic polymer in form of polyvinyl pyrrolidone in a methylene chloride solution also containing triethylenediamine, again by dipping and drying, followed by curing at 70° C. for 40 minutes. Then, the third step involves application of 20% of sodium chloride and 5% of polyvinyl pyrrolidone dissolved in water by a long-period dipping (one hour). The terminating drying is performed at 70° C. for a long period (eight hours).

By comparison it is possible by the method according to the invention as described in Example 1 to obtain a corresponding result by only a short dipping followed by air-drying and curing at 60° C. for one hour.

The hydrophilic polymer (b) may advantageously be a combination of a low-molecular hydrophilic polymer and a high-molecular hydrophilic polymer, such as 10 to 90% by weight of low-molecular hydrophilic polymer of a molecular weight of 20,000 to 50,000, combined with 90 to 10% by weight of high-molecular hydrophilic polymer of a molecular weight of 300,000 to 400,000. (All molecular weights are given as weight average molecular weights, in keeping with common practice in the art.)

The invention relates also to an article with a coating having friction-reducing properties in a wet condition, this coating comprising a binder (a), a hydrophilic polymer (b), and an osmolality-increasing compound (c), in which the article is characterised by the osmolality-increasing compound being present in form of particles of a size of a maximum of 50 μm, preferably maximum 30 μm, and most preferred maximum of 20 μm. Such a particle size ensures that the compound (c) is better dispersed in the coating compared to the coatings obtainable by the methods of Johansson et al., in which the osmolality-increasing compound (c) is precipitated during drying from a solvent in an uncontrolled manner.

The particles may advantageously be present in form of grains resulting from crushing or grinding of large crystals. As a result, sharp grains are obtained which surprisingly turn out to be able to form a stable suspension, whereby a uniform dispersion of the particles in the entire coating is ensured.

Regardless of how the particles are produced with the desired small particle size, it is of importance that the formation of crystals has substantially been performed prior to the coating process. In this manner, it is ensured that the coating of the article does not have an irregular dispersion of crystals of a nonuniform size. When the compound (c) comprises sodium chloride or a salt with a corresponding crystal structure, it is preferred that the particles have a substantially cubic crystal structure.

The article according to the invention has advantageously such a structure in which the particles of the compound (c) are uniformly dispersed in a matrix including the binder (a).

The article may furthermore be shaped such that the hydrophilic polymer (b) and the compound (c) are present in form of discrete particles in a matrix of the binder (a). It is furthermore possible that only a portion of the hydrophilic polymer (b) and the compound (c) are present in form of discrete particles in a matrix, where the matrix then includes both the binder (a) and the remaining portion of the hydrophilic polymer (b). Such structures render it possible to shape the article of any of the known hydrophilic polymers, as it is no longer necessary for the hydrophilic polymer to be soluble in the same solvent as the binder. In this manner, an improved possibility of providing designed coated articles has been obtained.

DETAILED DESCRIPTION OF PREFERRED EMBODIMENTS OF

The extent of applicability of the invention appears from the following detailed description. It should, however, be understood that the detailed description and the specific examples are merely included to illustrate the preferred embodiments, and that various alterations and modifications within the scope of protection will be obvious to persons skilled in the art on the basis of the detailed description.

As previously mentioned, the method according to the invention is used for providing a friction-reducing coating on articles, especially such articles intended for insertion into a body cavity.

Such articles are usually made of plastics, such as PVC or thermoplastic polyurethane, or of metal. An example thereof is a catheter usually made of PVC. Another example is trocar needles made of stainless steel.

Hydrophilic polymers cannot usually be bond directly onto such articles, and accordingly, it is necessary to include a binder in the coating material.

Any material can be used as binder, provided it provides a sufficient binding to the material of the article, and provided it is simultaneously able to retain the hydrophilic polymer.

Examples of binders meeting the above requirements are polyurethane, styrene-butadiene-rubber (SBR), and synthetic soluble elastomers. It is particularly advantageous to use a polyurethane which does not contain reactive isocyanate groups, particularly reactive isocyanate groups reacting with water while forming highly toxic aromatic amines. Particularly suited polyurethanes are thermoplastic polyurethanes made of di- or trifunctional isocyanates and a suitable polyol, such as a polyesterpolyol. A solution viscosity is usually indicated in commercially available polyurethanes instead of the molecular weight. Particularly suited polyurethanes have a viscosity for a 15% solution in methylethylketone of at least 300 cp and preferably 500 to 5,000 cp.

In order to obtain hydrophilic properties, which are important for a low friction in the wet condition of a coating, it is in principle possible to use any hydrophilic polymer, usually in form of a so-called hydrocolloid, Hydrocolloids are characteristic in forming gels when contacted with water and, accordingly, they have a viscosity-increasing effect. Hydrocolloids swell in a coating when the coating is wetted. Such a swelled coating has the desired low friction.

Examples of suitable hydrophilic polymers are poly-(N-vinyllactam), such as polyvinyl pyrrolidone (PVP), homopolymers of N-vinyl butyrolactam and N-vinyl caprolactam as well as copolymers of N-vinyl pyrrolidone, N-vinyl butyrolactam and/or N-vinyl caprolactam; other polyvinyl compounds, polysaccharides, hydrophilic polyurethanes, polyhydroxyacrylates and copolymers of vinyl compounds and hydroxyacrylates or acrylic acid. Particularly suited are polyethyleneoxide, polyvinyl pyrrolidone, heparin, dextran, xanthan, polyvinyl alcohol, hydroxypropyl cellulose, methyl cellulose, copolymers of vinyl pyrrolidone and hydroxyethylmethylacrylate or copolymers of methyl vinyl ether and maleic acid anhydride. Beyond polyvinyl pyrrolidone, particularly suited hydrophilic polymers are a copolymer of maleic acid and styrene produced by GAF (GAF Chemicals Corporation, Wayne, New Jersey, USA), a copolymer of maleic acid and vinyl ether, such as the one sold under the Trade Mark GANTREZ (GAF Chemicals Corporation, Wayne, New Jersey, USA), polyacrylate, polymethacrylate or polyethyleneoxide, such as the ones sold under the Trade Mark POLYOX TM (Union Carbide Corporation, Danbury, Connecticut, USA).

The hydrophilic polymer can advantageously be a combination of a low-molecular hydrophilic polymer (LHP) and a high-molecular hydrophilic polymer (HHP) in the ratio LHP:HHP of between 10:90 and 90:10, preferably between 75:25 and 45:55.

The use of a combination of low-molecular hydrophilic polymer and high-molecular hydrophilic polymer ensures that the resulting coating is provided with both the necessary solidity and the desired low friction. Thus, a high-molecular hydrophilic polymer can provide a solid coating, in turn providing in a wet condition a solid water film, which, however, still has a too high friction. By combining it with a low-molecular hydrophilic polymer, it is possible to obtain a reduction of the friction to the desired level. The above specified ratios of LHP:HHP are based on tests performed with polyvinyl pyrrolidone as the hydrophilic polymer. For polyvinyl pyrrolidone, a low-molecular polymer is defined having a molecular weight of 20,000 to 50,000, whereas a high-molecular hydrophilic polymer has a molecular weight of 300,000 to 400,000. When using other hydrophilic polymers, it cannot be excluded that numerical variations apply concerning the optimum LHP:HHP ratio and the molecular weights. Based on the information presented in this document, the person skilled in the art can, however, in such cases easily find the optimum ratio and the optimum molecular weights on the basis of a few tests followed by a selection based on the achieved solidity and adherence as well as the friction conditions.

Examples of suitable low-molecular hydrophilic polymers (LHP) are GANTREZ AN-119, GANTREZ AN-139, and GANTREZ AN-149 having molecular weights of 20,000; 41,000; and 50,000, respectively, as well as PVP K 30 with a molecular weight of about 40,000. All these low-molecular weight hydrophilic polymers are sold by GAF Chemicals Corporation.

Examples of high-molecular hydrophilic polymers (HHP) are PVP K 90 (molecular weight about 360,000; GAF Chemicals Corporation) and POLYOX TM WSR N-750 (molecular weight 300,000), POLYOX TM WSR N-3000 (molecular weight 400,000) and POLYOX TM WSR N-3333 (molecular weight 400,000) from Union Carbide Corporation.

The osmolality-increasing compound can be any compound ensuring the desired equalization of the osmotic pressure difference between the wetted coating and the surrounding body fluid. Such compounds are water-soluble compounds of a low molecular weight, preferably such compounds being dissociated in aqueous solution. Examples thereof are especially inorganic salts, such as sodium chloride, potassium chloride, potassium iodide, potassium nitrate, and calcium chloride or organic salts, such as sodium citrate. In principle, it is also possible to use other water-soluble compounds. Thus, it is also possible to use sodium benzoate, monoor disaccharides, such as glucose and sugar alcohols, such as sorbitol, which are all mentioned in U.S. Pat. No. 4,906,237. Such high-molecular or undissociated compounds are, however, less suited as the osmotic pressure obtained depends on the molar concentration or on the ion-concentration in case of dissociated compounds. Mono- and disaccharides are further disadvantageous in acting as nutritive media and microorganisms. In some cases where particular properties are required in the coating, the above or other less suited osmolality-increasing compounds can form part as the entire component (c) or as a portion of component (c), such as in combination with sodium chloride and potassium chloride. A further example is glycerol, which at the application can be used in emulsified condition, such as emulsified in a solution of the hydrophilic polymer.

All things considered, the requirements presented for the compound (c) are usually that it must be a low-molecular, physiologically acceptable water-soluble compound. The requirement concerning physiologically acceptable compounds applies, of course, only where it is relevant, such as in connection with articles intended to be inserted into body cavities.

When selecting the actual combination of binder (a), hydrophilic polymer (b), and osmolality-increasing compound (c), it is necessary to ensure that both component (a) and component (b) are soluble or, especially as far is component (b) is concerned, at least dispersable in the solvent used during the application of the coating material, whereas component (c) must preferably present a poor solubility in the solvent used and more preferred be substantially insoluble therein.

Component (c) must be insoluble in the solvent used because the volatility of the solvent after application of the coating depends highly on the presence of dissolved ingredients. Thus, if this osmolality-increasing compound, i.e., compound (c), is applied in form of an aqueous solution, as suggested in U.S. Pat. No. 4,906,237, the time necessary for removing the solvent, i.e., the water, constitutes a time-restricting factor for the entire process. The higher the concentration of the osmolality-increasing compound (c) is, the slower the evaporation of the water takes place. For instance, if the osmolality-increasing compound is glycerol, and the concentration thereof amounts to 50%, then the partial pressure of the water in the coating balances with the surroundings, provided the surroundings have a moisture content of 50%. Such a balance has the effect that no further evaporation of water from the coating takes place.

In addition, it is not possible to control the crystallization or the precipitation of the compound (c) and consequently, the dispersion thereof in the coating in the same manner as is allowed by application in suspended or emulsified form.

Thus, an essential advantage is obtained by component (c) being insoluble in the solvent used, as no change in particle size or shape takes place during the application and the drying of the coating. Correspondingly, component(c) does not migrate during the drying process, which might cause a non-uniform concentration of (c) in the dried coating.

When selecting the solvent, an advantage is obtained by selecting a solvent with a high volatility, whereby the solvent evaporates quickly after the application.

Examples of suitable solvents are ethylacetate, acetone, chloroform, methylethylketone, methylene chloride, ethylenechloride, methanol, ethanol, and mixtures thereof, preferably methylene chloride optionally mixed with a low amount of acetone, methylethylketone, methanol, ethanol or ethylacetate.

In some cases, the osmolality-increasing compound (c) can to some extent be soluble in the solvent used. Thus, in some cases it can be necessary to use a particular solvent or a particular combination of solvents in order to ensure the necessary solution of binder (a) and solution or dispersion of the hydrophilic polymer (b), where the compound (c) is more or less soluble in the solvent in question. In this case, an advantage is still obtained by not using water as solvent, and accordingly, it is still possible at least to a certain extent to obtain the advantages of the present invention.

The ratio of binder, such as polyurethane, and hydrophilic polymer, such as polyvinyl pyrrolidone, is, according to the known technique, cf. for instance WO publication No. 90/05162 and the Example of U.S. Pat. No. 4,906,237 (Johansson et al.), kept at 1:1.5 to 1:5, preferably 1:2.5 to 3.5, i.e. 1.5 to 5 and 2.5 to 3.5, respectively, parts by weight of hydrophilic polymer per part by weight of binder. While maintaining this ratio, it is not possible directly to use the method according to the invention including addition of an osmolality-increasing compound in dispersed condition contained in one or more coating materials of binder and/or hydrophilic polymer in dissolved or dispersed condition. Then, problems might easily arise concerning the coating not binding sufficiently to the coated article, or concerning the coating not achieving the desired low friction in wet condition.

It turned out, surprisingly, that an increase of the amount of hydrophilic polymer to more than 4 or 5 parts by weight per part by weight of binder, preferably more than 6 parts by weight, and especially more than 8 parts by weight of hydrophilic polymer per part by weight of binder, provides both a good adherence of the coating and simultaneously the desired low friction when the coating is performed in accordance with the present invention in one or a few steps while simultaneously applying the osmolality-increasing compound in dispersed condition.

A coating material only containing binder and hydrophilic polymer, i.e. without an osmolality-increasing compound, cannot usually obtain a satisfactory adherence of the coating, if the hydrophilic polymer exceeds 5 parts by weight per part by weight of binder on the other hand, the upper limit is usually found at 16, preferably 14, and particularly preferred 13 parts by weight of hydrophilic polymer per part by weight of binder when the coating material also contains the dispersed osmolality-increasing compound.

Beyond the possibility of applying the osmolality-increasing compound in undissolved condition by the method according to the invention, an additional advantage is thus found in the fact that the portion of hydrophilic polymer can be increased relative to the binder. This is, of course, an advantage as it is thereby easy to ensure the sufficient hydrophilic character of the total coating, even when only one coating step is involved.

Correspondingly, a particularly good hydrophilic character can be obtained by coating in several steps while forming several layers, as it is here possible to include a slightly lower portion of hydrophilic polymer in the first layer and then a higher portion in the succeeding layer.

The above specified ratios of hydrophilic polymer to binder are based on tests carried out using polyvinyl pyrrolidone (PVP) as hydrophilic polymer and polyurethane (PU) as binder. It cannot be excluded that numerical variations apply to the use of other hydrophilic polymers and/or other binders. In view of the common knowledge that the ideal ratio PU:PVP in the previously known coatings not containing suspended osmolality-increasing compound is 1:1.5 to 1:5, especially 1:2.5 to 1:3.5, whereas the incorporation of the suspended compound involves an ideal ratio of 1:4 to 1:16, especially 1:8 to 1:13, it is not, however, difficult for the person skilled in the art to find a suitable ratio of another combination of binder and hydrophilic polymer to be used together with the suspended compound based on common knowledge on suitable ratios for use without a suspended compound.

As an alternative embodiment of the invention, the osmolality-increasing compound, such as sodium chloride, is applied by way of powdering after the application of the polymer coating with the hydrophilic polymer and the binder. The powdering can be performed immediately after the application of the polymer coating. Prior to the powdering, the sodium chloride is subjected to crushing into a particle size of maximum 50 $\mu$m, preferably smaller than 30 $\mu$m, more preferably smaller than 15 $\mu$m. This embodiment, too, avoids the long drying period for the removal of water used as solvent, and the compound (c) can be uniformly dispersed across the surface of the coating.

When the method according to the invention is performed by the embodiment with the osmolality-increasing compound dispersed in the solvent used for dissolving the polymer ingredients, it is in practice possible to follow the procedure including the steps of producing a solution of the binder, usually together with the hydrophilic polymer or a portion thereof, in a common solvent, such as methylene chloride, which is an organic solvent in which the osmolality-increasing compound, such as sodium chloride, is insoluble.

In addition, a dispersion of the salt having the desired small particle size is produced. The dispersion may also include some adjuvants, such as up to 10% by weight calculated relative to the amount of salt. Examples of such adjuvants are AEROSIL ™ ($SiO_2$) (Degussa AG, Frankfurt, Germany). As the continuous phase, a fluid is used in which the salt is insoluble and which is compatible with the polymer solution. This fluid may for instance, be the same solvent as the one used for the polymer solution, i.e. especially methylene chloride. The dispersion should be as concentrated as possible so that sedimentation is prevented. As a result, such stability in the dispersion is ensured that it is possible without particular problems to use the same dispersion throughout an entire working-day. A concentrated dispersion ensures, furthermore, the advantage that the amount of methylene chloride to be evaporated after the application is kept as low as possible.

When the embodiment is used where the hydrophilic polymer (b) or a portion thereof is applied in a suspended, undissolved condition, the polymer can in a fine particle form be suspended together with the compound (c).

A very slim dipping vessel can be used for the coating process, the polymer solution and the salt dispersion being fed to the vessel through their respective feeding pipe so as to be mixed in a static mixer. The feeding can be performed at such a speed that a constant level is kept inside the dipping vessel.

After the application, the coated article is dried, preferably in two steps. The first step involves mild conditions, such as ordinary air-drying, in order to avoid a boiling up as well as formation of a dry membrane or film on the surface. Then, a drying is performed under comparatively stronger conditions, such as in an oven at 40° to 100° C., preferably 50° to 70° C. for a period of 20 to 120 minutes, preferably approximately one hour.

Usually, sterilization is finally performed after the packing of the article, in which either vapour and ethyleneoxide or electronic radiation is used.

EXAMPLE 1

The present Example illustrates the application of a coating having friction-reducing properties in wet condition on PVC tubing of a quality used in the production of catheters.

A coating material of the following composition was produced:
3.0 g of NaCl (100%)
0.9 g of polyurethane
4.6 g of polyvinyl pyrrolidone K30
4.6 g of polyvinyl pyrrolidone K90
74.8 g of methylene chloride
12.1 g of acetone The NaCl used has been crushed to a particle size of maximum 30 μm. The majority of the particles were of a particle size of about 10 μm.

Polyvinyl pyrrolidone K30 has a molecular weight of about 40,000 whereas polyvinyl pyrrolidone K90 has a molecular weight of about 360,000. They are both sold by GAF Chemicals Corporation, Wayne, N.J., USA.

| Salt/B + HP* | 30% by weight |
| --- | --- |
| PU:PVP = | 1:10 |
| LHP:HHP = 50:50 | |
| Dry matter content | 13.1% by weight |

*B = binder; HP = hydrophilic polymer.

The coating material was produced by NaCl initially being dispersed in a portion of methylene chloride, such as about 25 g. Then polyurethane was added dissolved in a sufficient amount of methylene chloride, to form a solution of 5 to 7% by weight of polyurethane in methylene chloride. Stirring was carried out, whereafter polyvinyl pyrrolidone K30 and K90 are added also dissolved in a sufficient amount of methylene chloride, and a stirring is performed. Finally, acetone was added. The coating material is produced at room temperature or at a lower temperature.

The PVC tubing to be coated was dipped into the coating material, whereafter it was air-dried until the methylene chloride had evaporated. Then, curing was carried out in an oven at 60 C for about one hour. After packing, the sample was finally sterilized in a conventional manner by means of vapour and ethyleneoxide.

The friction-reducing properties of the coating were evaluated partly by way of measuring the coefficient of friction of the wetted coating and partly by a subjective test, in which a test group of 5 persons evaluated the friction, the sliding properties, the adherence (the drying out), and surface irregularities in comparison with a commercial product—Lo-Fric—produced by Astra Tec. AB, Mölndalen, Sweden.

The coefficient of friction was measured by a modified method according to ASTM 1894-90. This method uses a sledge provided on the bottom side with two grooves in which two pieces of catheter can be secured. These two pieces of catheters have been wetted in advance by way of dipping into water. The sledge is arranged on a horizontal surface coated with wetted synthetic lambskin (wash leather), and the tensile force is measured which is necessary for pulling the sledge across the surface at a speed of 100 mm/min. The kinetic coefficient of friction is calculated on the basis of the measured force.

The above specified tubing was measured to have a coefficient of friction of 0.18, and the evaluation of the remaining properties revealed that it cannot be distinguished from the commercial comparison product.

The coatings appearing from the following Examples revealed similar results.

EXAMPLE 2

Like in Example 1, a PVC tubing of a quality used for the production of catheters was coated with the following coating material:
2.9 g of NaCl (100%) particle size less than 15 μm
0.64 g of polyurethane
4.5 g of polyvinyl pyrrolidone K30
4.5 g of polyvinyl pyrrolidone K90
75.4 g of methylene chloride
8.5 g of ethylacetate This coating material had the following composition:

| Salt/B + HP | 30% by weight |
| --- | --- |
| PU:PVP | 1:14 |
| LHP:HHP | 50:50 |
| Dry matter content | 13.1% by weight |

EXAMPLE 3

Like in Example 1, a PVC tubing of a quality used for the production of catheters was coated with the following coating material:
2 g of NaCl (100%)
0.9 g of polyurethane
4.6 g of GANTREZ AN-119*
4.6 g of POLYOX TM WSR N-3000**
74.8 g of methylene chloride
12.1 g of acetone
* molecular weight 20,000
** molecular weight 400,000

GANTREZ AN-119 is substantially insoluble in the used mixture, but provides a very stable dispersion in the fluid.

This coating material had the following composition:

| Salt/B + HP | 30% by weight |
| --- | --- |
| Binder: Hydrophlic polymer | 1:10 |
| LHP:HHP | 50:50 |
| Dry matter content | 13.1% by weight |

EXAMPLE 4

Like in Example 1, a PVC tubing of a quality used for the production of catheters was coated with the following coating material:
1.1 g of NaCl (100%)
1.1 g of polyurethane
6.6 g of polyvinyl pyrrolidone K90
70.9 g of methylene chloride
12.0 g of acetone This coating material had the following composition:

| Salt content (Salt/B + HP) | 14% by weight |
| --- | --- |
| PU:PVP | 1:6 |

Dry matter content    8.5% by weight

EXAMPLE 5

A PVC tubing of a quality used for the production of catheters was coated with the following coating material:
  1.1 g of polyurethane
  4.3 g of polyvinyl pyrrolidone K30
  4.3 g of polyvinyl pyrrolidone K90
  75.0 g of methylene chloride
  12.1 g of acetone After dipping into the coating material, the tubing was dried for a short period and then powdered with a mixture of equal amounts of KCl and NaCl. Then the coating was dried.

The completed coating had the following composition:

| Salt content (Salt/B + HP) | 30% by weight |
|---|---|
| PU:PVP | 1:8 |
| LHP:HHP | 50:50 |

EXAMPLE 6

Like in Example 1, a PVC tubing of a quality used for the production of catheters was coated with the following coating material:
  2.6 g of NaCl (100%)
  0.6 g of polyurethane
  4.9 g of polyvinyl pyrrolidone K30
  4.9 g of polyvinyl pyrrolidone K90
  74.3 g of methylene chloride
  12.1 g of acetone This coating material had the following composition:

| Salt content (Salt/B + HP) | 25% by weight |
|---|---|
| PU:PVP | 1:16 |
| LHP:HHP | 50:50 |
| Dry matter content | 13.5% by weight |

EXAMPLE 7

Like in Example 1, a PVC tubing of a quality used for the production of catheters was coated with the following coating material:
  2.6 g of KCl (100%)
  1.2 g of polyurethane
  9.6 g of polyvinyl pyrrolidone K30
  2.4 g of polyvinyl pyrrolidone K90
  72.0 g of methylene chloride
  12.1 g of acetone This coating material had the following composition:

| Salt content (Salt/B + HP) | 20% by weight |
|---|---|
| PU:PVP | 1:10 |
| LHP:HHP | 80:20 |
| Dry matter content | 15.8% by weight |

EXAMPLE 8

Like in Example 1, a PVC tubing of a quality used for the production of catheters was coated with the following coating material:
  2.5 g of NaCl (100%)
  1.1 g of polyurethane
  8.0 g of polyvinyl pyrrolidone K30
  3.4 g of polyvinyl pyrrolidone K90
  132.7 g of methylene chloride
  10.2 g of methyl acetate This coating material had the following composition:

| Salt content (Salt/B + HP) | 20% by weight |
|---|---|
| PU:PVP | 1:10 |
| LHP:HHP | 70:30 |
| Dry matter content | 9.5% by weight |

EXAMPLE 9

A trocar needle of stainless steel was coated with the following coating material:
  2.1 g of NaCl (100%)
  1.0 g of polyurethane
  2.9 g of polyvinyl pyrrolidone K30
  6.7 g of polyvinyl pyrrolidone K90
  75.3 g of methylene chloride
  12.1 g of acetone This coating material had the following composition:

| Salt content (Salt/B + HP) | 20% by weight |
|---|---|
| PU:PVP | 1:10 |
| LHP:HHP | 30:70 |
| Dry matter content | 12.7% by weight |

EXAMPLE 10

Like in Example 1, a PVC tubing of a quality used for the production of catheters was coated with the following coating material:
  3.2 g of NaCl (100%)
  0.9 g of polyurethane
  1.8 g of polyvinyl pyrrolidone K30
  7.3 g of polyvinyl pyrrolidone K90
  75.8 g of methylene chloride
  12.1 g of acetone This coating material had the following composition:

| Salt content (Salt/B + HP) | 32% by weight |
|---|---|
| PU:PVP | 1:10 |
| LHP:HHP | 20:80 |
| Dry matter content | 13.1% by weight |

EXAMPLE 11

Like in Example 1, a PVC tubing of a quality used for the production of catheters was coated with the following coating material:
  2.3 g of NaCl (100%)
  0.8 g of polyurethane
  10.7 g of POLYOX ™ WSR N-10*
  74.1 g of methylene chloride
  12.1 g of acetone

* molecular weight about 100,000.
This coating material had the following composition:

| Salt content (Salt/B + HP) | 20% by weight |
|---|---|
| PU:POLYOX | 1:14 |
| Dry matter content | 13.8% by weight |

EXAMPLE 12

Like in Example 1, a PVC tubing of a quality used for the production of catheters was coated with the following coating material:
2.3 g of glucose NaCl (100%)
0.8 g of polyurethane
10.7 g of POLYOX TM WSR N-10*
74.1 g of methylene chloride
12.1 g of methanol
  * molecular weight about 100,000
This coating material had the following composition:

| Glucose content (Glucose/B + HP) | 20% by weight |
|---|---|
| PU:POLYOX | 1:14 |
| Dry matter content | 13.8% by weight |

EXAMPLE 13

Like in Example 1, a PVC tubing of a quality used for the production of catheters is coated with the following coating material:
2.3 g of sorbitol (100%)
0.8 g of polyurethane
10.7 g of POLYOX TM WSR N-10*
74.1 g of methylene chloride
12.1 g of acetone
  * molecular weight about 100,000.
This coating material has the following composition:

| Sorbitol content (Sorbitol/B + HP) | 20% by weight |
|---|---|
| PU:POLYOX | 1:14 |
| Dry matter content | 13.8% by weight |

EXAMPLE 14

Like in Example 1, a PVC tubing of a quality used for the production of catheters is coated with the following coating material:
2.3 g of sodium citrate (100%) **
0.8 g of polyurethane
10.7 g of POLYOX TM WSR N-10*
74.1 g of methylene chloride
12.1 g of acetone
  * molecular weight about 100,000
  ** crushed into a particle size where 85% are $\leq 15$ μm.
This coating material has the following composition:

| Sodium citrate content (Sodium citrate/B + HP) | 20% by weight |
|---|---|
| PU:POLYOX | 1:14 |
| Dry matter content | 13.8% by weight |

In the completed coating, the crushed crystals appear as fine, uniformly dispersed grains in the coating. No changes have taken place, neither in shape nor in size.

EXAMPLE 15

Like in Example 1, a PVC tubing of a quality used for the production of catheters was coated with the following coating material:
2.6 g of NaCl (100%)
1.0 g of polyurethane
8.4 g of polyvinyl pyrrolidone K30
3.6 g of polyvinyl pyrrolidone K90
72.3 g of methylene chloride
12.1 g of acetone
This coating material had the following composition:

| Salt content (Salt/B + HP) | 20% by weight |
|---|---|
| PU:PVP | 1:12 |
| LHP:HHP | 70:30 |
| Dry matter content | 13% by weight |

In the dry coating on the PVC tubing, the salt appeared as uniformly dispersed cubic crystalline grains of the same shape and size as the starting material used in the coating material.

It was obvious from the above description of the invention that it can be varied in many ways. Such variations are not to be considered deviations from the scope and idea of the invention, and all such modifications obvious to persons skilled in the art are also to be considered covered by the following claims.

We claim:
1. A method for providing an article with a coating having friction-reducing properties when in a wet condition, comprising:
   applying to an accessible surface of said article a coating including a binder, a hydrophilic polymer and an osmolality-increasing compound, in which said osmolality-increasing compound, while being applied, is in a non-dissolved, solid, or liquid droplet condition, and in which said osmolality-increasing compound is applied using a technique selected from the group consisting of:
   (a) first applying one or more constituents of said coating to provide a layer, and thereafter, applying said osmolality-increasing compound as a powder onto said layer, and
   (b) including said osmolality-increasing compound in said coating as a suspension or emulsion in an organic solvent in which said osmolality-increasing compound is insoluble.
2. The method of claim 1, wherein:
   said coating, as applied, further includes a solvent in which said binder is dissolved, in which said hydrophilic polymer is at least one of dissolved and dispersed, and in which said osmolality-increasing compound is suspended.
3. The method of claim 2, wherein:
   said coating is applied as a plurality of superimposed layers.
4. The method of claim 1, wherein:
   said osmolality-increasing compound, as applied, has maximum particle size of 50 μm.
5. The method of claim 4, further comprising a preliminary step of converting said osmolality-increasing compound from crystals thereof, to particulate form, by crushing or grinding said crystals.

6. The method of claim 2, further comprising:
as a preliminary step, mixing together two theretofore separate coating portions to provide said coating immediately prior to said applying, in which:
(a) one of said portions comprises said binder dissolved in some of said solvent, and at least part of said hydrophilic polymer at least one of dissolved and dispensed in said same solvent; and
(b) the other of said portions comprises said osmolality-increasing compound suspended in some of said solvent, and optionally, a remaining part of said hydrophilic polymer at least one of dissolved and dispersed in said solvent.

7. The method of claim 1, wherein:
said coating contains 4 to 16 parts by weight of said hydrophilic polymer per part by weight of said binder.

8. The method of claim 1, wherein:
said coating contains 10 to 40 percent by weight of said osmolality-increasing compound relative to total weight of said binder and said hydrophilic polymer in said coating.

9. The method of claim 1, wherein:
10 to 90 percent by weight of said hydrophilic polymer has a weight average molecular weight of 20,000 to 50,000 and 90 to 10 percent by weight of said hydrophilic polymer has a weight average molecular weight of 300,000 to 400,000.

10. An article having an otherwise accessible surface coated with a coating having friction-reducing properties when in a wet condition, wherein:
said coating comprises a binder, a hydrophilic polymer and an osmolality-increasing compound, in which said osmolality-increasing compound is present as discrete solid, or liquid droplet particles having a maximum size of 50 $\mu$m.

11. The coated article of claim 10, wherein:
said particles have a substantially cubic crystal structure.

12. The coated article of claim 11, wherein:
said particles are sodium chloride crystals.

13. The coated article of claim 10, wherein:
said particles are uniformly dispersed in a matrix comprising said binder.

14. The coated article of claim 10, wherein:
said hydrophilic polymer and said osmolality-increasing compound are both present in said coating as discrete particles included in a matrix made of said binder.

15. The coated article of claim 10, wherein:
part of said hydrophilic polymer, and said osmolality-increasing compound are both present in said coating as discrete particles included in a matrix made of said binder and a remaining part of said hydrophilic polymer.

16. A coating composition for use in providing an article with a coating having friction-reducing properties when in a wet condition,
said coating composition comprising:
a binder, a hydrophilic polymer and an osmolality-increasing compound, in which said osmolality-increasing compound is in a non-dissolved, solid, or liquid droplet particulate condition having a maximum particle size of 50 $\mu$m.

* * * * *